(12) United States Patent
Subbalakshmi et al.

(10) Patent No.: US 7,115,572 B2
(45) Date of Patent: Oct. 3, 2006

(54) INDOLICIDIN ANALOGS WITH ANTI-MICROBIAL ACTIVITY

(75) Inventors: Chilukuri Subbalakshmi, Hyderabad (IN); Eruguraia Bikshapathy, Hyderabad (IN); Narasimhaiah Sitaram, Hyderabad (IN); Ramakrishnan Nagaraj, Hyderabad (IN)

(73) Assignee: Council of Scientific and Industrial Research, New Delhi (IN)

( * ) Notice: Subject to any disclaimer, the term of this patent is extended or adjusted under 35 U.S.C. 154(b) by 283 days.

(21) Appl. No.: 10/106,802

(22) Filed: Mar. 25, 2002

(65) Prior Publication Data

US 2004/0176300 A1 Sep. 9, 2004

Related U.S. Application Data

(60) Provisional application No. 60/279,789, filed on Mar. 29, 2001.

(51) Int. Cl.
*A61K 38/10* (2006.01)
*C07K 7/08* (2006.01)

(52) U.S. Cl. ......................... 514/14; 530/327

(58) Field of Classification Search ............ 514/14; 530/327
See application file for complete search history.

(56) References Cited

U.S. PATENT DOCUMENTS 6,180,604 B1 * 1/2001 Fraser et al. ............... 514/12

OTHER PUBLICATIONS

Subbalakshmi et al. Requirements for antibacterial and hemolytic activities . . . FEBS Letters. 1996, vol. 395, pp. 48-52.*
Subbalakshmi et al. Biochemical and Biophysical Research Communications. 2000, vol. 274, pp. 714-716.*

* cited by examiner

*Primary Examiner*—Jeffrey Edwin Russel
(74) *Attorney, Agent, or Firm*—Merchant & Gould P.C.

(57) ABSTRACT

The present invention relates to three single tryptophan analogs ILPWKLPLLPLRR-amide (IL4) (SEQ ID NO: 1), ILPLKLPWLPLRR-amide (IL8) (SEQ ID NO: 2) and ILPLKLPLLPWRR-amide (IL11) (SEQ ID NO: 3), of Indolicidin, a cationic tridecapeptide amide found in the granules of bovine neutrophils, the analogs having the amino acid only at the $4^{th}$, $8^{th}$ or $11^{th}$ position from the N-terminal, with leucine at its all other conventional positions, the analogs selectively having only anti-microbial activity and no hemolytic activity of Indolicidin, and thereby providing therapeutic options and a method thereof.

10 Claims, 3 Drawing Sheets

SEQUENCE LISTING

<160> NUMBER OF SEQ ID NOS: 4

<210> SEQ ID NO 1
<211> LENGTH: 13
<212> TYPE: PRT
<213> ORGANISM: Bos taurus

<400> SEQUENCE: 1

Ile Leu Pro Trp Lys Leu Pro Leu Leu Pro Leu Arg Arg
1               5                   10

<210> SEQ ID NO 2
<211> LENGTH: 13
<212> TYPE: PRT
<213> ORGANISM: Bos taurus

<400> SEQUENCE: 2

Ile Leu Pro Leu Lys Leu Pro Trp Leu Pro Leu Arg Arg
1               5                   10

<210> SEQ ID NO 3
<211> LENGTH: 13
<212> TYPE: PRT
<213> ORGANISM: Bos taurus

<400> SEQUENCE: 3

Ile Leu Pro Leu Lys Leu Pro Leu Leu Pro Trp Arg Arg
1               5                   10

<210> SEQ ID NO 4
<211> LENGTH: 13
<212> TYPE: PRT
<213> ORGANISM: Bos taurus

<400> SEQUENCE: 4

Ile Leu Pro Trp Lys Trp Pro Trp Trp Pro Trp Arg Arg
1               5                   10

INDOLICIDIN ANALOGS WITH ANTI-MICROBIAL ACTIVITY

CROSS-REFERENCE TO RELATED APPLICATION

This application claims priority of U.S. patent application Ser. No. 60/279,789, filed 29 Mar. 2001.

FIELD OF INVENTION

The present invention relates to three single tryptophan analogs ILPWKLPLLPLRR-amide (IL4) (SEQ ID NO: 1), ILPLKLPWLPLRR-amide (IL8) (SEQ ID NO: 2) and ILPLKLPLLPWRR-amide (IL11) (SEQ ID NO: 3), of Indolicidin, a cationic tridecapeptide amide found in the granules of bovine neutrophils, said analogs having said amino acid only at 4th, 8th or 11th position from N-terminal, with leucine at its all other conventional positions, said analogs selectively having only anti-microbial activity and no hemolytic activity of Indolicidin, and thereby providing therapeutic options and a method thereof.

BACKGROUND AND PRIOR ART REFERENCES

Indolicidin (IL) is a 13-residue anti-microbial peptide having the sequence ILPWKWPWWPWRR-amide (SEQ ID NO: 4). It is present in the cytoplasmic granules of bovine neutrophils.(1)

The presence of five tryptophans out of 13-residues renders its amino acid composition unique among host-defense endogenous anti-microbial peptides. It is cationic due to the presence of two arginines and one lysine and exhibits broad-spectrum anti-microbial activity.

The peptide also causes lysis of erythrocytes (2) and is cytotoxic to human and rat T lymphocytes. (3)

Binding of IL to anionic and neutral lipid vesicles and leakage of entrapped contents from lipid vesicles have been observed. (4,5)

In aqueous medium, IL is unordered (5,6). Even in media of low dielectric constant, Circular Dichroism spectra suggests that a large fraction of the molecules populate unordered conformation.

However, the spectra in trifluoroethanol and sodium dodecyl sulphate micelles have been assigned to polyproline and type VI beta-turn by different groups (6,7). Proline residues are not essential for the biological activities of IL, as a variant where P has been replaced A by shows comparable activities to IL. (8)

Publication (8) by Applicant shows that in Indolicidin where proline was replaced by alanine and tryptophan by phenylalanine has anti-bacterial activity comparable to Indolicidin. Also, they showed that presence of tryptophan appears to be essential for hemolytic activity as the phenylalanine analogs does not exhibit any hemolytic activity. But, there is more work to be done to overcome the hurdles to understand the behaviour of various possible analogs. Also further research is needed to be done to determine the stability of various possible analogs.

Further, it is important to have analogs that have absolutely no hemolytic activity even at an extremely high concentration. This will determine the safety profile of various possible analogs.

Also anti-microbial activity of various possible analogs is most important. The said activity is to be comparable to Indolicidin and at the same time with no hemolytic activity.

OBJECTS OF THE PRESENT INVENTION

The main object of the present invention is to develop novel analogs of Indolicidin.

Another object of the present invention is to develop analogs of Indolicidin with selective anti-microbial activity.

Yet another object of the present invention is to develop analogs of Indolicidin with no hemolytic activity.

Further object of the present invention is to determine the structure of the Indolicidin analogs in various mediums.

Another object of the present invention is to develop a method of preparing Indolicidin analogs.

Yet another object of the present invention is prepare a composition to comprising single tryptophan analogs of Indolicidin and pharmaceutically acceptable additives.

Further object of the present invention is to develop a method to treat animals and human beings for anti-microbial infections.

SUMMARY OF THE INVENTION

The present invention relates to three single tryptophan analogs ILPWKLPLLPLRR-amide (IL4) (SEQ ID NO: 1), ILPLKLPWLPLRR-amide (IL8) (SEQ ID NO: 2) and ILPLKLPLLPWRR-amide (IL11) (SEQ ID NO: 3), of Indolicidin, a cationic tridecapeptide amide found in the granules of bovine neutrophils, said analogs having said amino acid only at 4th, 8th or 11th position from N-terminal, with leucine at its all other conventional positions, said analogs selectively having only anti-microbial activity and no hemolytic activity of Indolicidin, and thereby providing therapeutic options and a method thereof.

DETAILED DESCRIPTION OF THE PRESENT INVENTION

Accordingly, the present invention relates to three single tryptophan analogs ILPWKLPLLPLRR-amide (IL4) (SEQ ID NO: 1), ILPLKLPWLPLRR-amide (IL8) (SEQ ID NO: 2) and ILPLKLPLLPWRR-amide (IL11) (SEQ ID NO: 3), of Indolicidin, a cationic tridecapeptide amide found in the granules of bovine neutrophils, said analogs having said amino acid only at 4th, 8th or 11th position from N-terminal, with leucine at its all other conventional positions, said analogs selectively having only anti-microbial activity and no hemolytic activity of Indolicidin, and thereby providing therapeutic options and a method thereof.

In an embodiment of the present invention, said analogs showing type1 β-turn structure in trifluoroethanol.

In another embodiment of the present invention, said analogs showing type1 β-turn structure in sodium dodecyl sulphate micelles.

In yet another embodiment of the present invention, said analogs showing greater ordered conformation in trifluoroethanol as compared to sodium dodecyl sulphate micelles.

In still another embodiment of the present invention, said analogs showing unordered structure in aqueous medium.

In an embodiment of the present invention, a method of producing three single tryptophan analogs of Indolicidin namely, ILPWKLPLLPLRR-amide (IL4) (SEQ ID NO: 1), ILPLKLPWLPLRR-amide (IL8) (SEQ ID NO: 2) and ILPLKLPLLPWRR-amide (IL11), (SEQ ID NO: 3), a cationic tridecapeptide amide found in the granules of bovine neutrophils, said analogs having said amino acid only at position 4, 8 or 11 from N-terminal, with leucine at its all other conventional positions, said analogs having selective anti-microbial activity and no hemolytic activity of Indolicidin, providing therapeutic options thereof.

In another embodiment of the present invention, IL 4 is a tridecapeptide with amino-acids sequence of Isoleucine-Leucine-Proline-Tryptophan-Lysine-Leucine-Proline-Leucine-Leucine-Proline-Leucine-Arginine-Arginine (SEQ ID NO: 1).

In yet another embodiment of the present invention, IL 8 is a tridecapeptide with amino-acids sequence of Isoleucine-Leucine-Proline-Leucine-Lysine-Leucine-Proline-Tryptophan-Leucine-Proline-Leucine-Arginine-Arginine (SEQ ID NO: 2).

In still another embodiment of the present invention, IL 11 is a tridecapeptide with amino-acids sequence of Isoleucine-Leucine-Proline-Leucine-Lysine-Leucine-Proline-Leucine-Leucine-Proline-Tryptophan-Arginine-Arginine (SEQ ID NO: 3) .

In another embodiment of the present invention, synthesizing the peptide sequence of said analogs with C-terminal amide.

In yet another embodiment of the present invention, purifying said peptides using conventional methods.

In a further embodiment of the present invention, a composition useful for treating microbial infections, said composition comprising one or more single tryptophan analogs of Indolicidin having amino-acid sequence of ILPWKLPLLPLRR-amide (IL4) (SEQ ID NO: 1), ILPLKLPWLPLRR-amide (IL8) (SEQ ID NO: 2) and ILPLKLPLLPWRR-amide (IL11) (SEQ ID NO: 3), with said amino acid at positions 4, 8 and 11 respectively from N-terminal and optionally pharmaceutically acceptable additives.

In another embodiment of the present invention, wherein said additives are selected from a group of nutrients comprising proteins, carbohydrates, sugar, talc, magnesium stearate, cellulose, calcium carbonate, starch-gelatin paste, and/or pharmaceutically acceptable carrier, excipient, diluent, or solvent.

In still another embodiment of the present invention, wherein concentration of analogs is ranging between 2–200 µg/ml.

In still another embodiment of the present invention, wherein ratio of analogs and additives is ranging between 1:10 to 10:1.

In still another embodiment of the present invention, wherein said composition is in form of an ointment, cream, capsule, tablet, syrup, concentrate, powder, granule, aerosol, and/or beads.

In a further embodiment of the present invention, a method of treating microbial infections using composition comprising one or more single tryptophan analogs of Indolicidin having amino-acid sequence of ILPWKLPLLPLRR-amide (IL4) (SEQ ID NO: 1), ILPLKLPWLPLRR-amide (IL8) (SEQ ID NO: 2) and ILPLKLPLLPWRR-amide (IL11) (SEQ ID NO: 3), with said amino acid at positions 4, 8 and 11 respectively from N-terminal and optionally pharmaceutically acceptable additives, said method comprising steps of administering said composition to a subject.

In another embodiment of the present invention, wherein said method is used for treating animals and human beings.

In yet another embodiment of the present invention, wherein said composition is administered orally, or inhaled.

In still another embodiment of the present invention, wherein said composition shows no adverse effect on health.

In still another embodiment of the present invention, wherein said composition shows anti-microbial activity.

In still another embodiment of the present invention, wherein said composition shows no hemolytic activity of Indolicidin.

In still another embodiment of the present invention, wherein tryptophan is essential for hemolytic activity.

In another embodiment of the present invention, all the single tryptophan analogs exhibit anti bacterial activity. However unlike indolicidin, they do not lyse erythrocytes.

In yet another embodiment of the present invention, structure analysis by Circular Dichrosim Spectroscopy indicate that the analogs are unordered in aqueous medium and adapt β-turn structures in trifluroethanol and micelles.

In still another embodiment of the present invention, the tryptophan residues in indolicidin are to be essential for hemolytic activity but not antibacterial activity.

The non-specific biological activities of indolicidin and specific anti bacterial activity of single tryptophan analogs suggests that in short peptides, a motif composed of hydrophobic amino acids with the exception of tryptophan, interspaced with proline residues and cationic amino acids at the N and C termini would favour selective antibacterial activity.

In still another embodiment of the present invention, the said three analogs of IL are synthesized using the Multipin Peptide Synthesis kit from Chiron Technologies. (8)

Fmoc-amide-handle crowns which would yield peptides with C-terminal amides and Fmoc chemistry are employed for the synthesis of peptides. (9)

In still another embodiment of the present invention, the synthetic peptides are cleaved and deprotected using 95% trifluoroacetic acid (TFA) containing 5% of 1:3 mixture of ethanedithiol (EDT) and thioanisole (TA) for 16–18 h at room temperature.

In still another embodiment of the present invention, cleaved peptides are purified on Hewlett Packard 1100 series high pressure liquid chromatography (HPLC) instrument using a µ Bondapak $C_{18}$ column (3.9×300 mm) (Waters).

In still another embodiment of the present invention, the solvent system consisted of aqueous 0.1% TFA as mobile phase A and 0.1% TFA in acetonitrile as solvent B. A linear gradient from 15–60% B in A, with a flow rate of 1 ml/min is used, with peak detection at 280 nm.

In still another embodiment of the present invention, peptides are characterized by matrix assisted laser desorptioh ionization time of flight mass spectreometry.

In still another embodiment of the present invention, the antimicrobial activities of the peptides are determined in liquid medium by a modified method described by Lehrer et al. (10)

In still another embodiment of the present invention, all incubations are carried out at 37° C. Microbial growth is determined by measuring the increase in $OD_{600}$.

The lowest concentration of the peptide that result in complete inhibition of growth is recorded as its minimal inhibitory concentration (MIC).

In still another embodiment of the present invention, the microorganisms used are *Escherichia coli* (W160.37) and *Staphylococcus aureus*. A peptide concentration in stock solution is determined by amino acid analysis.

In still another embodiment of the present invention, hemolytic activity of the peptides is assessed on freshly isolated rat erythrocytes.

In still another embodiment of the present invention, heparinized rat blood in saline is initially centrifuged at 1000 rpm for 10 min to remove the buffy coat.

In still another embodiment of the present invention, the erythrocyte suspension is further washed thrice with 5 mM Hepes, pH 7.4 containing 150 mM NaCl.

In still another embodiment of the present invention, aliquots of cell suspension (~$10^6$ cells) in eppendorf tubes are incubated with the peptide in duplicates at 37° C. for 30 min with gentle mixing.

In still another embodiment of the present invention, the tubes are then centrifuged and the absorbance of the supernatants is measured at 540 nm. The lysis obtained with 1% triton×100 is taken as 100%.

In still another embodiment of the present invention, Circular Dichroism (CD) spectra are recorded in 5 mM Hepes pH 7.4, trifluoroethanol (TFE) and micelles of sodium dodecylsulfate (SDS) (10 mM), on a Jasco J-715 automatic recording spectropolarimeter at 25° C. using a quartz cell of 1 mm path length.

Calibration is carried out with d-camphorsulfonic acid. Data are represented as mean residue ellipticities.

In still another embodiment of the present invention, the biological activities of IL and the L analogs are summarized in Table 1.

TABLE I

Antibacterial activity and hemolytic Activity of Indolicidin and its analogs

| Peptide | E.COII (MIC µg/ml) | S.aureus (MIC µg/ml) | % Hemolytic activity at 100 µg/ml |
|---|---|---|---|
| IL | 5 | 2 | 100[a] |
| IL4 | 15 | 10 | 0 |
| 1L8 | 20 | 10 | 0 |
| IL11 | 20 | 5 | 0 |

[a]100% hemolytic activity is observed beyond 70 µg/ml.

In still another embodiment of the present invention, all the single trp analogs show activity against E.COII and S. aureus but with slightly reduced potency as compared to IL. However, unlike IL, they do not exhibit hemolytic activity against rat erythrocytes even at 100 µg/ml.

In still another embodiment of the present invention, the total elimination of hemolytic activity of said analogs came as a surprise.

In still another embodiment of the present invention, the selective anti-microbial activity is a unique phenomenon. Though the MIC was comparatively more than the original IL but the selectivity obtained is a more desired characteristic and also difficult to achieve.

BRIEF DESCRIPTION OF THE ACCOMPANYING DRAWINGS

Figure 1:
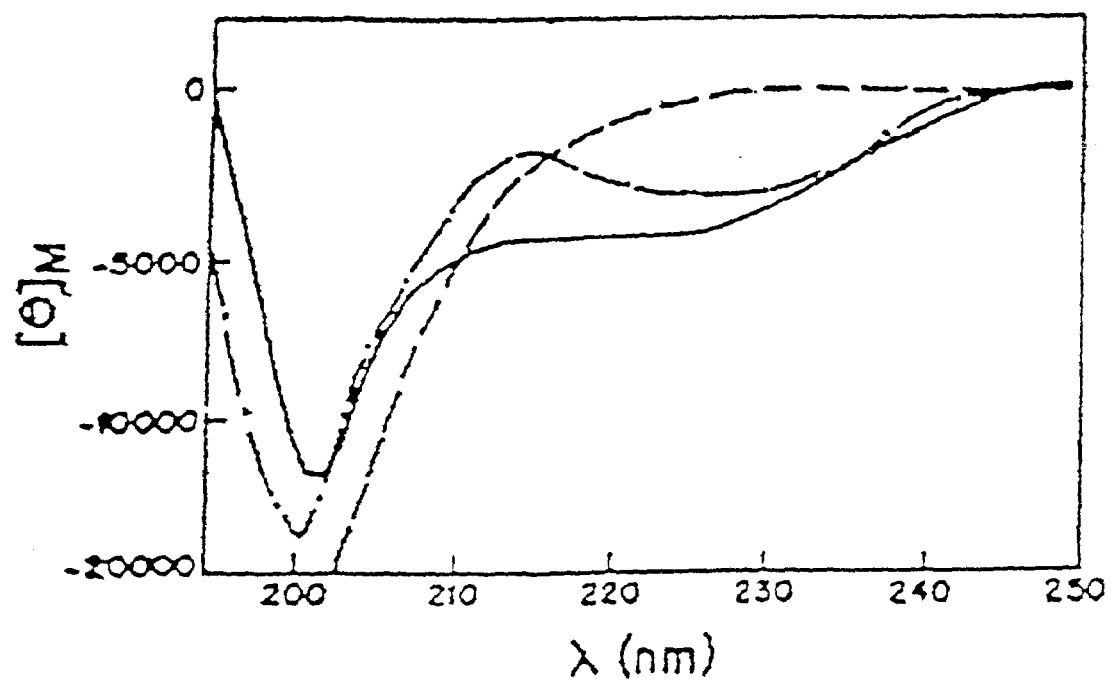
FIG. 1 shows CD spectra of IL4 with following mediums: (i) TFE (_____), (ii) micelles of sodium dodecyl sulfate (. _____ .), (iii) buffer ( - - - ).
Figure 2:
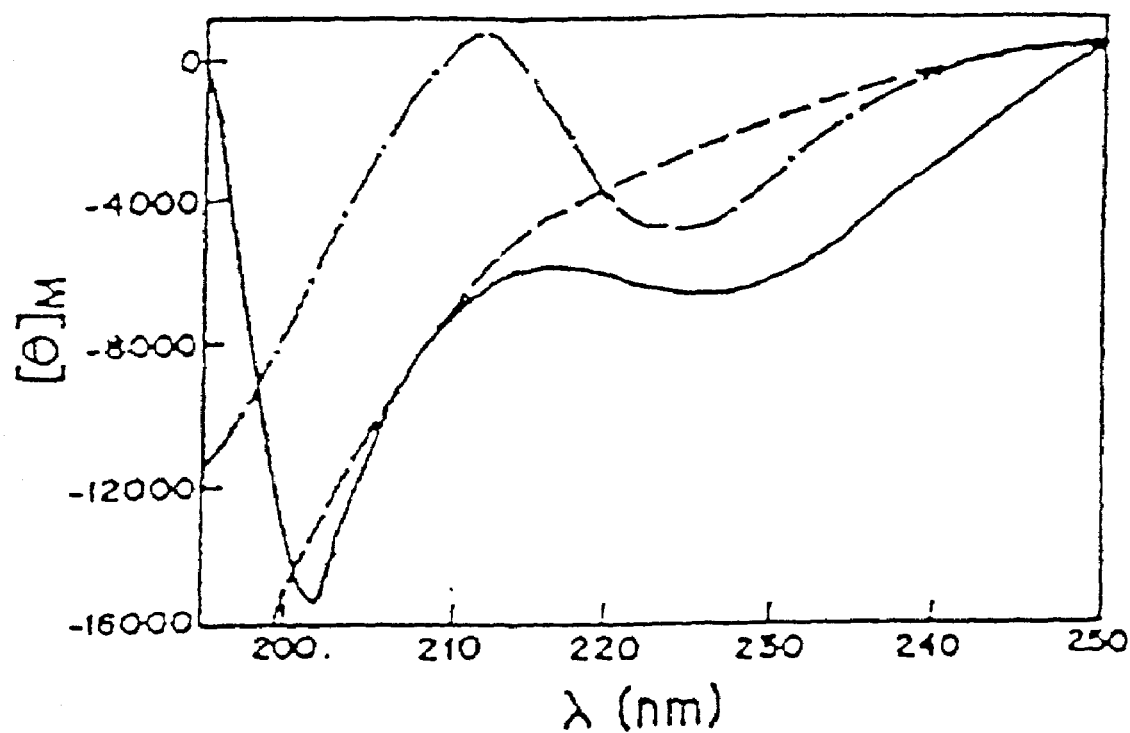
FIG. 2 shows CD spectra of IL8 with following mediums: (i) TFE (_____), (ii) micelles of sodium dodecyl sulfate (. _____ .), (iii) buffer ( - - - ).
Figure 3:
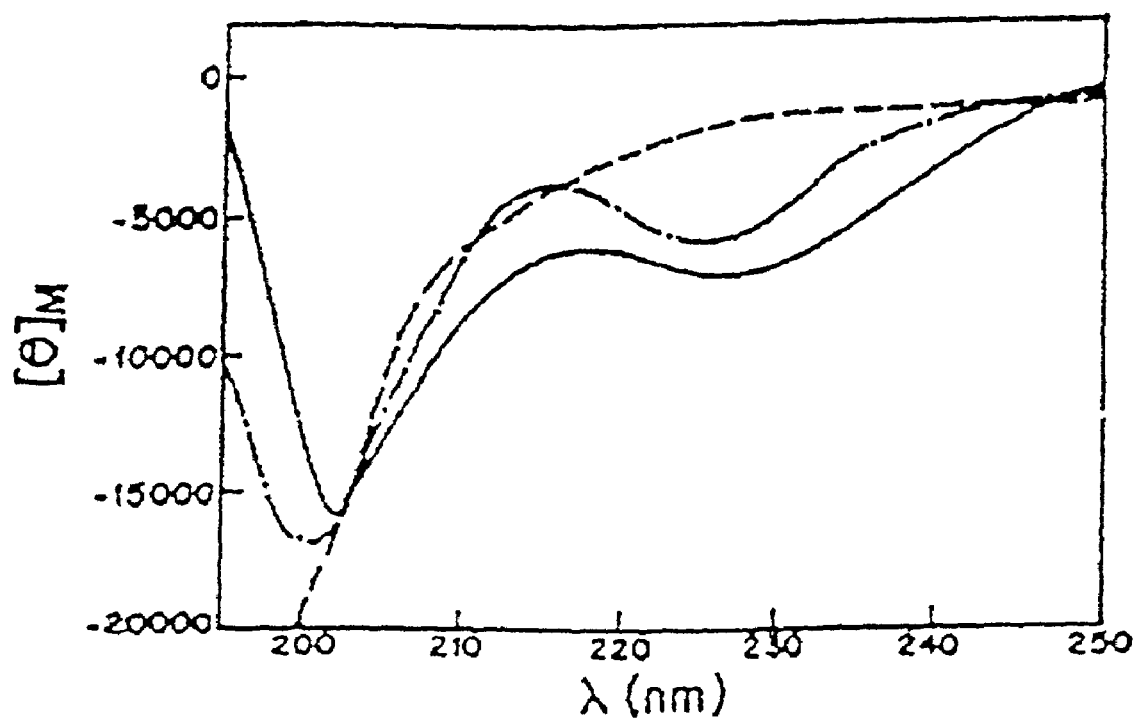
FIG. 3 shows CD spectra of IL11 with following mediums: (i) TFE ( _____ ) (ii) micelles of sodium dodecyl sulfate (. _____ .), (iii) buffer ( - - - ).

In still another embodiment of the present invention, the CD spectra of IL4, IL8 and IL11 (FIGS. 1, 2, and 3) in buffer, TFE and SDS micelles are clearly illustrates the invention.

In still another embodiment of the present invention, in buffer, the spectra are characteristic of peptides in unordered conformation.

In still another embodiment of the present invention, the spectra in TFE resemble those of class C spectral pattern of model peptides adopting type1 beta-turn conformation. (11, 12)

In still another embodiment of the present invention, it is unlikely that the peptides adopt alpha-helical or $3_{10}$ helical conformation due to the presence of 3 proline residues.

In still another embodiment of the present invention, the spectra in SDS micelles also suggest type1 beta-turns.

In still another embodiment of the present invention, ccomparison with the TFE spectra suggests that there is relatively greater proportion of molecules in unordered conformation in SDS micelles.

In still another embodiment of the present invention, turn conformations have been assigned to an all L analog of IL as well as single tryptophan analogs similar to the ones in the present study but with A instead of R in the $12^{th}$ position. (7)

In still another embodiment of the present invention, the spectra of the single tryptophan analogs clearly do not represent polyproline conformation.

The conformation properties of single tryptophan analogs of IL with A instead of R at the $12^{th}$ position have been studied by CD.(7) However, their biological activities have not been investigated In still another embodiment of the present invention, the data presented in this study indicate that the tryptophans in IL are not essential for its antimicrobial activity, but are necessary for hemolytic activity. (8)

In still another embodiment of the present invention, while there are two views regarding the conformation of IL (6,7), a polyproline structure is clearly not necessary for biological activity, especially antibacterial activity.

In still another embodiment of the present invention, the amino acid tryptophan has a strong preference for the membrane interface as compared to other hydrophobic amino acids (13, 14).

In still another embodiment of the present invention, in spite of high affinity for membranes, IL appears to exert its antimicrobial activity by mechanisms other than permeabilization of bacterial cytoplasmic membranes. (15, 16)

In still another embodiment of the present invention, inhibition of DNA synthesis by IL in E.COII at concentrations at which RNA and protein synthesis are either partially or not affected at all has been observed.

In still another embodiment of the present invention, the non-specific cytolytic activity of IL and specific antibacterial activity of analogs where W has been replaced by L or F (8) indicates that a string of tryptophans in a short relatively flexible peptide chain is a motif that favors cytolytic activity against eukaryotic cells.

In still another embodiment of the present invention, a motif of hydrophobic amino acids, with the exception of multiple tryptophans, interspersed with proline residues and cationic amino acids at the N or C termini can have selective activity on bacteria.

In still another embodiment of the present invention, incorporation of non-coded amino acids like norleucine, homoleucine and norvaline would provide stability against proteases and such peptides could possibly have therapeutic potential.

The invention claimed is:

1. Three single tryptophan analogs of Indolicidin having amino-acid sequence of ILPWKLPLLPLRR-amide (IL4) (SEQ ID NO: 1), ILPLKLPWLPLRR-amide (IL8) (SEQ ID NO: 2) and ILPLKLPLLPWRR-amide (L11) (SEQ ID NO: 3), with said amino acid at positions 4, 8 and 11 respectively from N-terminal.

2. Analogs as claimed in claim 1, wherein said analogs have amino acid leucine in place of tryptophan at its all other conventional positions.

3. Analogs as claimed in claim 1, wherein said analogs have Type1 β-turn structure in trifluroethanol.

4. Analogs as claimed in claim 1, wherein said analogs have Type1 β-turn structure in sodium dodecyl sulphate micelles.

5. Analogs as claimed in claim 1, wherein said analogs have more ordered conformation in trifluroethanol than in sodium dodecyl sulphate micelles.

6. Analogs as claimed in claim 1, wherein said analogs have unordered structure in aqueous medium.

7. A method of producing three single tryptophan analogs of Indolicidin having amino-acid sequence of ILPWKL-PLLPLRR-amide (IL4) (SEQ ID NO: 1), ILPLKLPWL-PLRR-amide (IL8) (SEQ ID NO: 2) and ILPLKLPLLP-WRR-amide (SEQ IL11) (ID NO: 3), with said amino acid at positions 4, 8 and 11 respectively from N-terminal, said method comprising:
  (i) synthesizing peptide sequence of said analogs with C-terminal amide, and
  (ii) purifying synthesized sequence using High Performance Liquid Chromatography HPLC.

8. An antibacterial method comprising contacting bacteria with one or more single tryptophan analogs of Indolicidin having an amino-acid sequence ILPWKLPLLPLRR-amide (IL4) (SEQ ID NO: 1), ILPLKLPWLPLRR-amide (IL8) (SEQ ID NO: 2) and ILPLKLPLLPWRR-amide (IL11) (SEQ ID NO: 3), with said amino acid at positions 4, 8 and 11 respectively from N-terminal.

9. A method as claimed in claim 8, wherein the analogs show no hemolytic activity of Indolicidin.

10. A method as claimed in claim 8, wherein tryptophan is essential for hemolytic activity.

* * * * *